United States Patent [19]

Johnson

[11] 4,009,617
[45] Mar. 1, 1977

[54] ON-LINE LIQUID SAMPLERS

[76] Inventor: Julius Theodore Johnson, 348 - 20th St. SE., Cedar Rapids, Iowa 52403

[22] Filed: Mar. 18, 1976

[21] Appl. No.: 667,971

[52] U.S. Cl. .......................... 73/422 TC; 417/520
[51] Int. Cl.² ........................................ G01N 1/14
[58] Field of Search ................ 73/422 R, 422 TC; 417/375, 379, 496, 472, 520

[56] References Cited

UNITED STATES PATENTS

| | | | |
|---|---|---|---|
| 3,229,527 | 1/1966 | Johnson | 73/422 |
| 3,371,617 | 3/1968 | Klootwyk | 417/520 |

*Primary Examiner*—S. Clement Swisher
*Attorney, Agent, or Firm*—Johnston, Keil, Thompson & Shurtleff

[57] ABSTRACT

Sampling apparatus for periodically withdrawing small samples of liquid flowing through a pipe. The apparatus embodies an intake passage communicating with a T-section in the pipe. Liquid in the intake passage is pumped by a diaphragm which is pulsed pneumatically at periodic intervals. A check valve in the intake passage has one end projecting into the diaphragm chamber and is pushed positively by the diaphragm to intake port-closing position. A second passage communicating with the intake passage has a pop valve which opens under the diaphragm-created pressure after the check valve closes. Each periodic sample is collected from the latter passage in a plastic bag or other container. The apparatus can be washed and sanitized while on line by hose and coupling unit placed on the apparatus.

8 Claims, 11 Drawing Figures

U.S. Patent  Mar. 1, 1977  Sheet 1 of 3  4,009,617
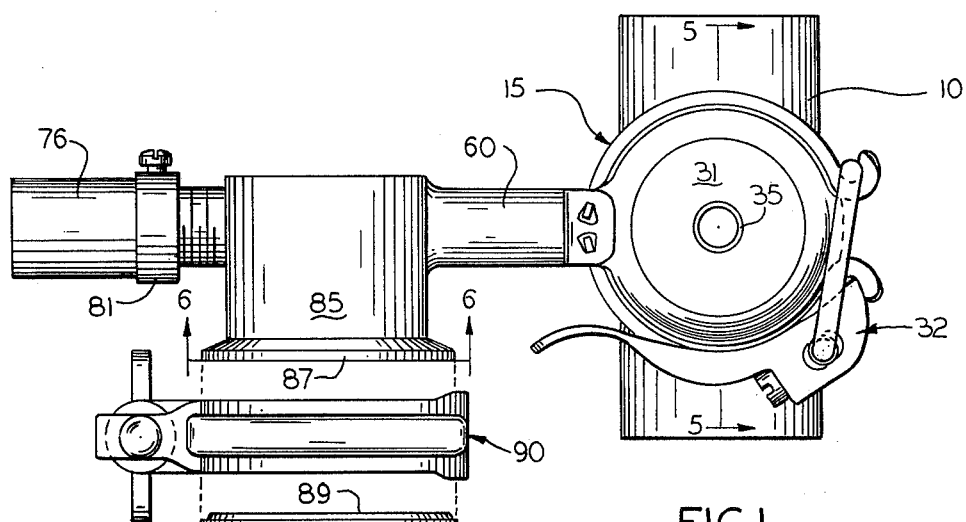
FIG.1
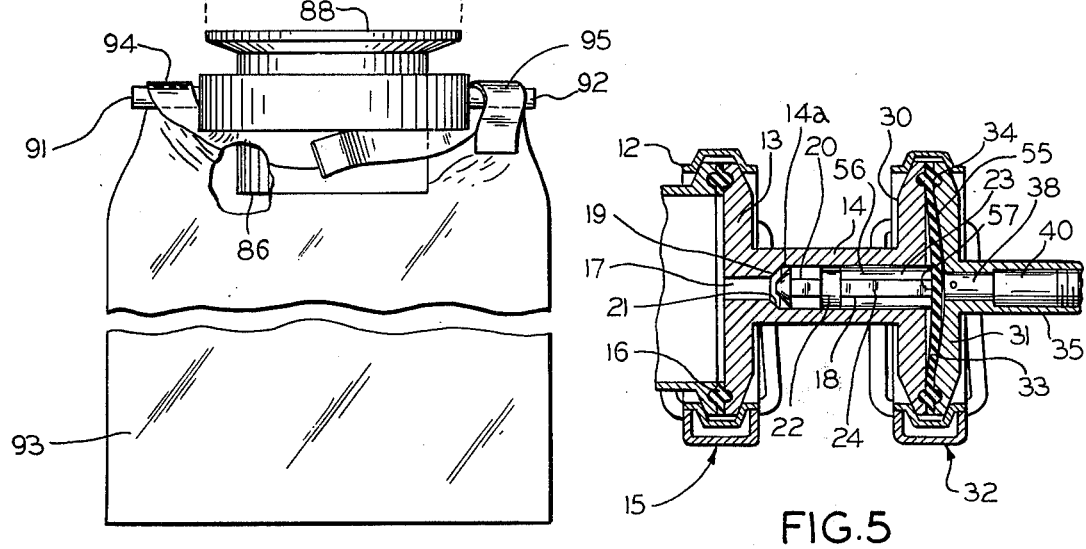
FIG.5
FIG.2

ON-LINE LIQUID SAMPLERS

INTRODUCTION

This invention relates in general to improvements in liquid sampling apparatus of the general type described and illustrated in my U.S. Pat. No. 3,229,527, issued Jan. 18, 1966. The invention relates to apparatus for the accurate sampling of liquids as they flow through pipes or conduits.

The subject sampling apparatus is particularly useful for the sampling of liquids of non-uniform composition, e.g., liquids which stratify into layers of different composition.

Liquids, such as milk, present problems in accurate sampling inasmuch as the samples must be taken from various portions of the milk in representative amounts in order that the total sample is accurately representative of the total body of milk which is sampled. When milk is pumped from a tank truck into a dairy plant, the quality of the milk, particularly its average butterfat content, must be ascertained as well as the volume or weight of the milk in order to determine the overall value of the milk trucked to the dairy plant.

The most convenient way to sample milk is to withdraw samples of the milk as it is pumped through a conduit or pipe from the tank truck into the dairy. A small portion of milk is withdrawn from the pipe at predetermined, equally spaced increments of milk flowing through the pipe, such increments being either by weight or by volume. When the milk is drawn out of a tank truck with the outlet near the bottom of the tank, the first portions of the milk will be considerably lower in butter fat content than the last portion of the milk pumped into the dairy plant.

By withdrawing small samples of equal volume at equally spaced increments by volume or weight of the milk during its flow through a conduit or pipe and collecting the withdrawn samples, the total sample is collected which is closely representative of the average composition of the entire body of milk pumped through the pipe or conduit, e.g., from a tank truck through a pipe into a dairy plant.

THE INVENTION

The sampling apparatus of my U.S. Pat. No. 3,229,527 and the sampling apparatus of this invention have, in communication with a pipe or conduit through which the milk is pumped, a small orifice into which milk can flow as it is pumped through the conduit. This small orifice communicates with a sampling chamber which can fill with a constant volume of milk. Periodically, preferably in response to a measurement by weight or by volume of milk flowing through the conduit, the sampling chamber is emptied, and the milk sample emptied from the sampling chamber is collected. The sampling chamber is then allowed to fill again with milk whereby another representative sample is obtained. By repeating this cycle over a regular sequence, preferably in a sequence corresponding to equal increments by weight or volume of the milk flowing through the conduit, an aggregate representative sample is obtained over the entire flow cycle.

The sampling apparatus herein utilizes a diaphragm disc to attain the pumping action which (a) moves a valve into passage closing position, and (b) creates the pressure for overcoming the spring-load bias of another valve in a second passage in communication with the first-mentioned passage. The latter valve is preferably of the pop valve type. The inner side of the diaphragm forms a movable wall of the sampling chamber. When the diaphragm is moved inwardly into the sampling chamber by air pressure against its outer surface, the pressure created by the movement of the diaphragm forces the check valve to shift to a position to block communication through the small orifice between the sampling passage and the milk conduit or line. The pressure also activates the pop valve to move it to non-blocking relationship between the sampling passage and the discharge passage. This, in turn, allows a given volume of liquid to flow out of the sampling passage into the discharge passage, from which it is collected.

When the air pressure on the outer side of the diaphragm is released, it returns to normal position. When the pressure in the sampling passage drops to a value at which the liquid pressure force drops below the bias force of the spring of the pop valve, the pop valve moves back to blocking relationship between the sampling passage and the discharge chamber. The pressure in the main milk line moves the check valve into non-blocking position between the small orifice and the sampling passage and the sampling chamber again fills with milk entering it through the small orifice.

The filling and dumping of the sampling chamber is done in a short time interval and the sampling apparatus stays dormant over a period of time. After a given interval, the diaphragm is again moved by air pressure and the aforedescribed sampling cycle is repeated.

Particular improvements in the subject sampling devices include:

a. a check valve in the sampling passage having its diaphragm-contiguous end projecting into the diaphragm chamber;

b. constructions of the sampling devices in segments held together by quick release clamps for ready disassembly, cleaning and/or servicing of the sampling device;

c. quick connection and detachment of plastic sample-receiving bags or threaded neck bottles to the sampling apparatus;

d. valve components which can be readily disassembled and cleaned and/or serviced;

e. pop valve structures with a bevel-seated plug for isolating threaded parts of the pop valve passage from contact with the liquid sample;

f. constructions of the sampling devices allowing quick connections of flushing, cleansing and sanitizing connections when the piping is flushed; and g. constructions of sampling devices which can be mounted by T-connections on vertical, angular or horizontal segments of the piping of a plant.

THE ILLUSTRATED EMBODIMENT

Preferred embodiments of the invention are illustrated in the drawings, wherein:

FIG. 1 is a partly exploded, side elevation of a T-connection for a liquid-conducting pipe with a first embodiment of the sampling apparatus of the invention mounted thereon;

FIG. 2 is a front elevation of the same embodiment and T-connection;

FIG. 5 is a section view taken on section plane 5—5 of FIG. 1;

The illustrated on-line sampling devices are preferred embodiments to be mounted on a liquid-conveying pipe by a T-connection. The devices have an intake passage extending radially with reference to the pipe and axially relative to T-leg, the passage having a small entrant port. A check valve is axially slidable in said passages. The valve seat is contiguous to the entrant port. At the other end of the passage is a diaphragm port. A flexible diaphragm extends across said chamber, forming a movable wall of said chamber. The check valve has an end portion projecting into the diaphragm chamber, whereby said check valve is moved to closed position by the pumping movement of the diaphragm. A discharge passage extends laterally from the intake passage. Pneumatic means applies air pressure against the diaphragm at spaced intervals. The check valve seats against the valve seat, resulting in a build-up of liquid pressure in the chamber and first passage. A pop valve in the discharge passage opens when the build-up of pressure occurs in the intake passage. The diaphragm chamber has a frusto-conical wall on the pneumatic side. The pneumatic means may embody a restricted port in the center of the frusto-conical wall or may have a movable valve body having a tip portion which is pressed against the center of the diaphragm by the air pulse, said body having lateral ports for admitting pressurized air to the diaphragm chamber when its tip portion is in the extended position. In either case, the initial air pulse immediately pushes the check valve to closed position before there is substantial overall movement of the diaphragm.

Figure 3:
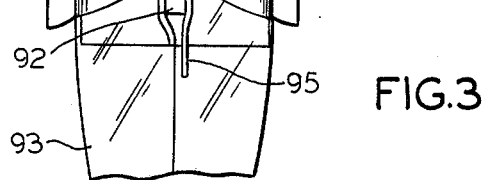
FIG. 3 is a rear elevation of the same embodiment and the T-connection.

Referring to the drawings, the embodiment illustrated in FIGS. 1–3 has the sampling device mounted on a T-section 10, which in turn is mounted in the piping system through which flows the liquid to be sampled. The lateral leg 11 of the T-section has a flange 12. A disc 13, which is integral with and coaxial with a tube 14 is held opposed the face of the flange 12 by a quick release clamp ring 15 of generally known construction. A circular gasket 16 between the face of the flange and the face of the disc provides a fluid-tight joint.

The disc 13 and tube 14 have an axial sample intake port 17 of smaller diameter than the inside passage 14a of the tube 14. A check valve 18 is axially movable in the passage 14a over a limited distance. As shown in FIG. 5, the tapered valve head 19 may, under fluid pressure in the T-section 10, move away from the beveled edge 21 of the intake port 17 to allow entry of fluid into the passage 14a via the port 17.

The portion of the check valve adjacent the head 19 is cylindrical but has two or more flat sides 20 which allow fluid to flow into the void between the passage 14a and the neck section 22 of the valve. The valve stem 23 is of cylindrical configuration but also has two or more flattened sides 24 along which sampled liquid can flow.

The pumping chamber of the sampling device is provided at the opposite end of the tube 14 by the opposed discs 30 and 31. Disc 30 is integral with and coaxial with the tube 14. The disc 31 is held in opposed relationship to the disc 30 by the clamp ring 32 of known construction.

Figure 11:
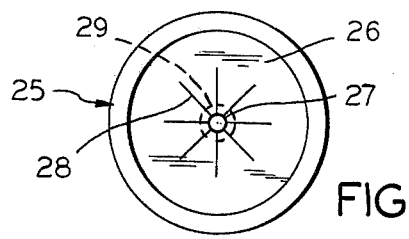
FIG. 11 is a plan view of the disc of another diaphragm chamber.

A circular, elastomer diaphragm 33 has its peripheral bead 34 seated in opposed grooves of the opposed faces of the discs 30 and 31 to form a fluid-tight seal. In the embodiment of FIG. 11, the pneumatic side disc 25 has a frusto-conical face 26 in the center of which is a small air discharge port 27. Small air flow grooves 28 may radiate from the port. The initial air pulse, supplied through tube 29, e.g., at 60 – 100 psi., impinges on the diaphragm opposite the check valve and drives it immediately to closed position.

Figure 9:
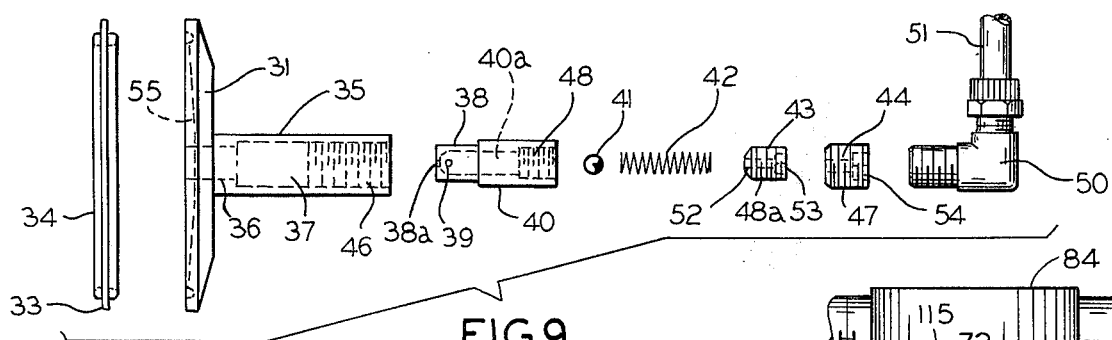
FIG. 9 is an exploded view of the pneumatic segment of the apparatus by which the diaphragm is moved by air pressure.

Referring to FIGS. 5 and 9, the pneumatic part of the sampling device embodies a tubular section 35 which is integral with and coaxial with the disc 31. Its air passage comprises the axial passage 36 and a concentric, larger diameter axial passage 37.

The cylindrical tip 38 of a check valve body 40 is slidably positioned in, and is longer than, the passage 36. An axial passage 40a extends through the check valve body 40 to the end wall of the tip 38. Lateral ports 39 allow air to be passed against the pneumatic or back side of the diaphragm 33, i.e., the side of the diaphragm facing the disc 31, after the valve body has been driven by the initial air pulse to a position where its tip portion enters the diaphragm chamber, striking the diaphragm and immediately pushing the check valve to closed position.

A ball 41 of smaller diameter than the passage 40a is held by the pressure of the spring 42 against the port 38a in the end wall of tip portion 38. The spring retainer 43 is an Allenhead screw whose threads 48a are threaded into the internal threads 48 of the passage 40a, the spring pressure on the ball 41 being adjustable by the degree of threading. The assembly of the check valve body 40, the ball 41, the spring 42 and the retainer 43 is held in the tubular section 35 by the Allenhead screw 44, whose external threads 47 are threaded into the internal threads of the tube section 35. The elbow connector 50 for the pneumatic air line 51 is also threadly connected to the internal threads 46 of the tube section 35. To activate the diaphragm, air is admitted under pressure to the line 51. This creates a positive pressure on the back side of the diaphragm 33 via the axial passages 52, 53 and 54 through screws 43 and 44 and ports 39.

As will be noted particularly in FIG. 5, the face 55 of the disc 31 is frusto-conical. The pressurized air first drives valve unit 40 so that its tip 38 pushes the center portion of the diaphragm 33 away from the frusto-conical wall 55, thereby immediately pushing the check valve 18 to closed position and exposing lateral ports 39. Air from these ports then presses the diaphragm against the flat face of disc 30 to complete the pumping stroke. On the return stroke, after release of the air pressure, air is vented first through ports 39 and, at the end of the return stroke, through the port 38a.

The stem 56 of the check valve 18 always projects into the diaphragm chamber in all embodiments of the invention. When the diaphragm is pressed against the frusto-conical wall 26 or 55 by the liquid pressure in passage 14a, the end of the stem 56, with the valve in fully retracted, open position, has only a slight clearance with the retracted diaphragm. The initial air pulse (FIG. 11) or the tip 38 of the valve 40 immediately pressures the center portion of the diaphragm against the valve stem 56 to provide positive, immediate movement of the check valve 18 to closed position, i.e., the seating of beveled head 19 on the beveled valve seat 21. This relationship assures substantially constant volume liquid displacement on the liquid side of the diaphragm 33 during the pumping stroke.

Removal of sample from the tube section 14 is achieved through the take-off tube 60 having an axial passage 61 in communication with the tubular passage 14a. A tubular passage 62 of larger diameter than the passage 61 is also provided coaxially in the take-off tube 60. A beveled valve seat 63 is formed at the juncture of the passages 61 and 62.

When fluid pressure occurs within the passage 61, the valve head 64 moves away from the valve seat 63 with the valve stem 65 sliding in the passage 62. The valve includes a cylindrical rod extension 66 projecting into and occupying a substantial percent of the volume of the passage 61. This cylindrical rod extension has the advantage of substantially decreasing the fluid volume capacity of the passage 61. This leads to more accurate samples and a quicker response in the flow of liquid per pulse of the diaphragm by decreasing the accumulated volume within the passage 61.

The segment 67 of the valve stem 65 has a clearance with the inner wall of passage 61. Its head 64 is substantially cylindrical but has two or more flat sides 68 which permit fluid to flow past the head. The rear portion 69 is in sliding but substantially fluid-tight contact with the inner wall of the passage 61, whereby the valve stem 65 is slidably borne by the rear portion 69 and the contacting parts of the head 64.

Liquid which flows past the valve stem section 67 enters the clearance between the intermediate segment 71 of the stem and the wall of the passage 61. It then flows through the outlet passage 72 into the sample collecting portion of the apparatus.

The pop valve structure is provided by a spring bias of the valve stem 65, urging the valve stem onto the valve seat 63. A cap 76 houses and compresses a spring 77 which is fitted about the rear stem 70 of the slidable valve stem 65. The rear portion of the take-off tube 60 has external threads 79 on which internal threads 78 are threaded to the desired degree of compression of the spring 77. A setscrew 80 in the threaded collar 81 fixes the collar 81 in the desired adjusted position of spring-compression, the cap 76 being threaded into abutting contact with the collar 81. Spring compression changed if there is a change in air pressure in the system connected to line 51.

The sample collection section of the apparatus comprises cylindrical member 84 formed integrally with the tube 60. Its tubular collar 85 extends downwardly. Increments of sampled liquid flow under pressure out of passage 72. The collar 85 has a removably attached thereto a tubular sample bag attaching unit 86. The removable attachment is provided by the opposed flanges 87 and 88 of the parts 85 and 86 detachably held with the ring gasket 89 therebetween by the screw clamp 90 of known construction.

The sample bag attaching unit 86 has a pair of opposed, diametrically outwardly extending rods or bars 91, 92. A plastic bag 93 has its neck portion fitted about the tubular bag attaching unit 86. The bag also has closure strips, the tabs 94 and 95 of which are wrapped about the rods or bars 91, 92 to hold the sample bag in place during the sampling operation.

Liquid flowing through the pipe in which the T-section 10 is connected is periodically sampled by applying, at predetermined intervals, air pressure via the air supply conduit 51. A device suitable for this purpose is shown in my U.S. Pat. No. 3,229,527.

The inner side of the diaphragm forms a movable wall of the sampling chamber. When the diaphragm is moved inwardly into the sampling chamber by air pressure against its outer surface, the pressure created by the movement of the diaphragm forces the check valve to shift to a position to block communication through the small orifice between the sampling passage and the milk conduit or line. The pressure also activates the pop valve to move it to non-blocking relationship between the sampling passage and the discharge passage. This, in turn, allows a given volume of liquid to flow out of the sampling passage into the discharge passage, from which it is collected.

When the air pressure on the outer side of the diaphragm is released, it returns to normal position. When the pressure in the sampling passage drops to a value at which the liquid pressure force drops below the bias force of the spring of the pop valve, the pop valve moves back to blocking relationship between the sampling passage and the discharge chamber. The pressure in the main milk line moves the check valve into non-blocking position between the small orifice and the sampling passage and the sampling chamber again fills with milk entering it through the small orifice.

Upon initiation of the air pressure pulse, the diagram 33 moves from its concavo-convex shape as shown in FIG. 5 under the increasing pressure between the pneumatic side of the diaphragm and the concave face 55 of the disc 31. As the diaphragm moves toward the flat face of the disc 30, the check valve 18 is moved positively by the diaphragm until it is seated on the valve seat 21. In so moving the check valve 18, the diaphragm causes pressure to be built up in the tubular section 14. When the check valve reaches its closed position, the liquid pressure in the tubular section 14 and the take-off tube 60 (ahead of the valve seat 63) builds up sufficiently to cause the pop valve to open. Liquid then flows past the head 64 and section 67 in the valve stem 65 and is discharged into the passage 72. The section 71 of the valve stem is dimensioned and positioned so that it substantially moves entirely across the outlet passage 72 when the valve is popped. The volume of each sample portion per pulse corresponds substantially to the displaced volume of the diaphragm's movement in the diaphragm chamber.

Figure 8:
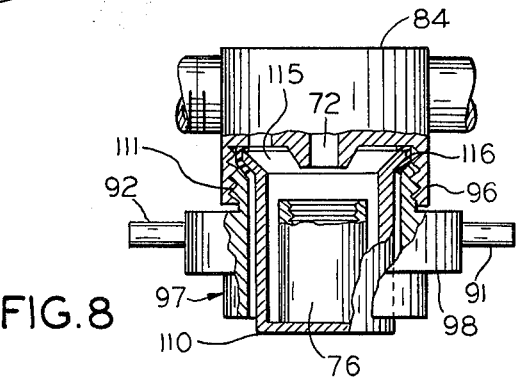
FIG. 8 is a fragmentary side elevation of a portion of the apparatus, partly in diametric section, with a washing cup utilized in lieu of the plastic sampling bag during the washing procedure.

Alternatively, the sample collecting unit may be a unit such as shown in FIG. 8. Here the collar 96 is internally threaded. A threaded neck bottle (not shown) may be mounted in the collar to collect the samples, or, as illustrated, a sample bag attaching unit 97 may be mounted therein. The unit 97 has a collar 98 from which project the tab-receiving bars or rods 91, 92.

Figure 7:
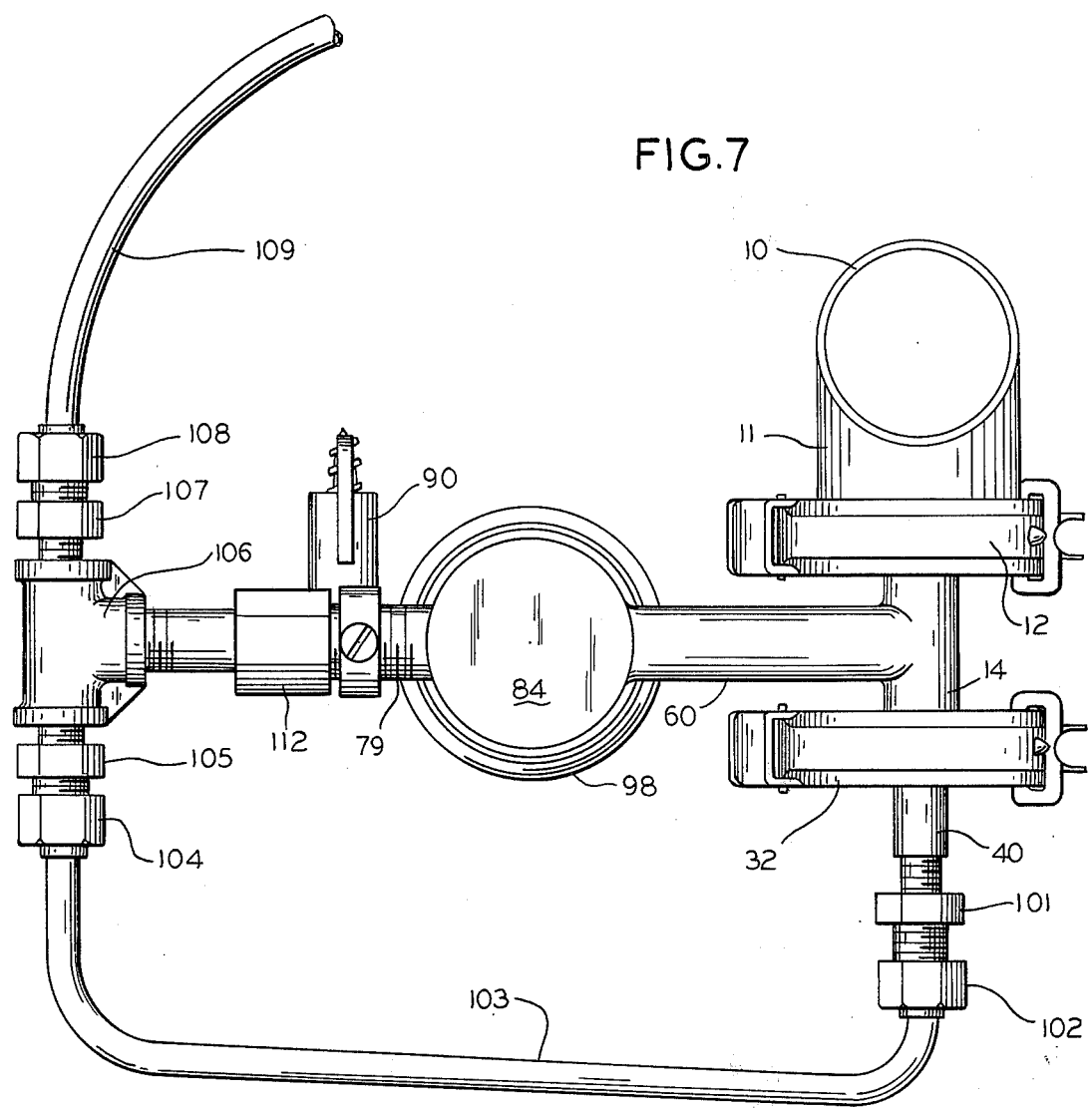
FIG. 7 is a top plan view of the embodiment of FIGS. 1–6 in which washing connections are attached to the sampling device.

For washing or flushing the sampling apparatus for sanitary reasons and/or for clearing the sampling apparatus of accumulated liquid, the washing apparatus of FIG. 7 and FIG. 8 may be attached. The diaphragm 33 is removed. The elbow 50 of the air pressure line 51 is removed from the check valve body unit 40 and in its place is connected an adaptor 101 with a hose connector 102. A hose 103 runs to another hose connector 104, which in turn is connected by an adaptor 105 to a T-section 106. The latter is threaded on the threads 79 of the take-off tube 60 by a coupler 112, which replaces the cap 76.

The T-section 106 is in turn connected by an adaptor 107 and a hose connector 108 to the hose 109, from which the wash liquid is discharged into a sewer or recycled to the low pressure side of the pump used for the wash cycle. During the washing operation, a cup 110 having a flared upper end 115 is slipped into the T-section 85a. When the attaching unit 86a is threaded into the T-section, its upper end compresses a ring gasket 116 against the flared end 115 of the cup to provide a fluid-tight seal. Particularly in cases where a sanitizing wash fluid is used, it is advantageous to place the removed cap 76 and (if desired) the removed diaphragm 33 inside the cup. Instead of cup 110 and collar 97, the washing may be done with a threaded cup (not shown) screwed into threads 111.

Washing liquid from the piping enters the tubular section 14. It divides therein, a part flowing past the check valve and through the diaphragm chamber and port 27 or port 38a, through tube 35 and then into hose 103. The other part flows through the tube 60 past the pop valve (whose spring pressure has been removed) and out of port 72 into the cup 110. The pop valve is positioned by the connector 112 abutting against rod 70 so that pop valve is unseated by the liquid pressure but the neck segment 71 is still aligned with the port 72.

Figure 6:
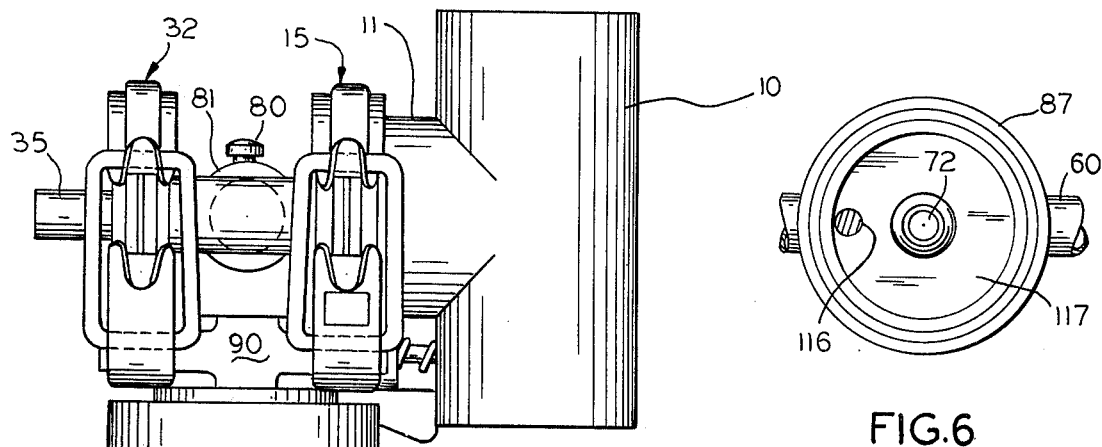
FIG. 6 is a plan view as viewed from plane 6—6 of FIG. 1.
Figure 4:
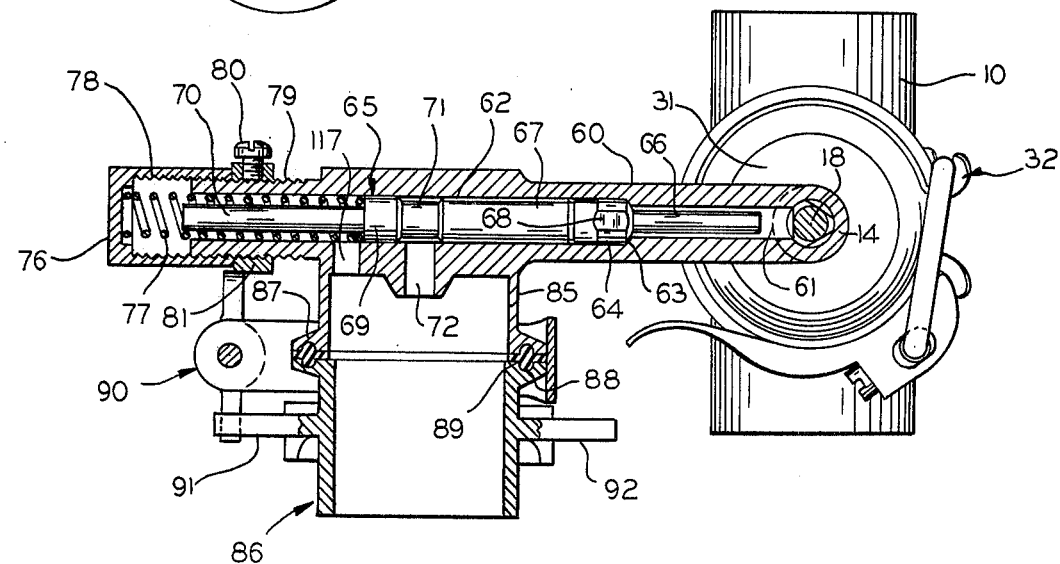
FIG. 4 is a section view of the embodiment of FIGS. 1–3 on section plane 4—4 of FIG. 2.

Liquid flows through the cup 110 and out of the vent hole 116 (FIGS. 4 and 6) in the bottom wall 117 of the cylindrical part 84, which is on the side of the liquid-tight segment 69 opposite to that of the port 72. It then flows out of the tube 61 via connector 112 to the tee 106, from which all wash liquid flows through tube 109.

Figure 10:
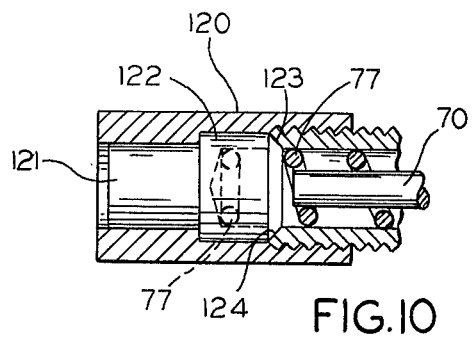
FIG. 10 is a fragmentary section of the outer end of a modified form of the pop valve.

The embodiment of FIG. 10 employs, in lieu of collar 81 and cap 76, a sleeve 120 threaded on the threads 79 of the tubular discharge member 60. It has a removable plug 121 seated therein. The head 122 of the plug has a tapered seat 123 seated against the tapered end 124 of the member 60 to prevent any liquid which may have passed the segment 69 from accumulating in the threaded parts. The spring 77 seats against or in the head 122. Its pressure cannot be varied as in the case of the cap 76 except by changing the plug length.

It is thought that the invention and its numerous attendant advantages will be fully understood from the foregoing description, and it is obvious that numerous changes may be made in the form, construction and arrangement of the several parts without departing from the spirit or scope of the invention, or sacrificing any of its attendant advantages, the forms herein disclosed being preferred embodiments for the purpose of illustrating the invention.

The invention is hereby claimed as follows:

1. A sampling device for periodically withdrawing small samples of a liquid flowing through a pipe, which device comprises a sample intake member having a sample intake passage, an entrant port at one end of said intake passage, and a diaphragm pumping chamber at the opposite end of said intake passage; said diaphragm pumping chamber having a flexible diaphragm extending thereacross and subdividing said chamber into a pneumatic side and liquid pumping side, the latter being in communication with said intake passage; means for periodically applying pneumatic pressure to the pneumatic side of said chamber; a check valve axially slidable in said intake passage; a valve seat in said intake passage adjacent said port; a valve head on one end of said check valve seatable in said valve seat upon axial movement of said check valve toward said port; said check valve having its opposite end projecting into said chamber and in contact with said diaphragm whereby said check valve is moved positively by said diaphragm during its pumping stroke to port-closing position when pneumatic pressure is applied to said diaphragm, said valve and said intake passage having spaced portions therebetween for flow of liquid into and through said passage into said chamber; a sample discharge member having a sample discharge passage communicating with said intake passage; valve means in said discharge passage adapted to open upon build-up of liquid pressure in said intake passage and diaphragm chamber during said pumping stroke of said diaphragm; and means on said sample discharge member for collecting the increments of samples of liquid withdrawn from said pipe by said sampling device.

2. A sampling unit as claimed in claim 1, wherein the wall of said chamber on its pneumatic side is a frusto-conical wall against which said diaphragm lies when said check valve is open and said intake passage is at the liquid pressure of the liquid in said pipe.

3. A sampling unit as claimed in claim 1, wherein the wall of said chamber on its pneumatic side is a frusto-conical wall against which said diaphragm lies when said check valve is open and said intake passage is at the liquid pressure of the liquid in said pipe, said pneumatic means embodying a tube projecting from and communicating with the center of said wall, a hollow valve slidably mounted in said tube and having a cylindrical tip portion, said hollow valve being slidable to a position wherein its tip portion projects into said chamber when pneumatic pressure is applied, said tip portion thereby contacting the center of said diaphragm and pushing said center portion away from said wall, a plurality of lateral ports in the cylindrical wall of said tip portion, and said hollow valve further being slidable to a retracted position with its tip portion retracted from said chamber when said diaphragm rests against said wall of said chamber, whereby said tip portion pushes the center portion of said diaphragm away from said wall upon initiation of a pneumatic pulse, after which air exits from said lateral ports and continues to push said diaphragm away from said wall of said chamber to provide the pumping stroke of said diaphragm.

4. A sampling device as claimed in claim 3, said tip portion having an end wall with a pot therein, and a spring-loaded ball check valve seated in said port to allow air in said chamber to escape therefrom when said diaphragm is pressed against said wall upon release of the pneumatic pressure.

5. A sampling device as claimed in claim 1, said discharge passage and its valve means comprising a discharge tube intercepting said intake passage at a right angle, a sample discharge port for discharging liquid sample from said discharge passage, a valve seat in said discharge passage between said sample discharge port and said intake passage, a pop valve having a valve head and a valve stem, said stem extending across said discharge port, spring means biasing said valve to closed position with said head seated on said seat, said valve stem and discharge tube having clearances for flow of liquid along said stem to said discharge port when said valve is opened by liquid pressure overcoming the bias of said spring means, and means on said stem providing a substantially liquid tight seal with the wall of said discharge passage beyond said discharge port.

6. A sampling device as claimed in claim 5, said valve in said discharge passage having a rod projecting from said head toward said intake passage, said rod having a clearance with the wall of the intake passage and thereby reducing the free volume of liquid in the portion of said discharge passage between said valve seat and said intake passage.

7. A sampling device as claimed in claim 1, wherein said means for collecting the increments of samples comprises a collar removably attached by a clamp to said discharge member; rods projecting from said collar and a sample-collecting bag attached to said collar by tabs wrapped about said rods.

8. A sampling device as claimed in claim 1, and a washing unit composed of hoses, couplings and a cup mounted on said device, and means to provide a circuit for flowing washing fluid, after removal of said diaphragm, through a first branch including said intake passage, and said diaphragm chamber, and through a second branch including said discharge passage with flow into and out of said cup.

* * * * *